US011833118B2

(12) United States Patent
Boeckl et al.

(10) Patent No.: US 11,833,118 B2
(45) Date of Patent: *Dec. 5, 2023

(54) ENCAPSULATION OF LIPOPHILIC INGREDIENTS IN DISPERSIBLE SPRAY DRIED POWDERS SUITABLE FOR INHALATION

(71) Applicant: Flurry Powders, LLC, Tarpon Springs, FL (US)

(72) Inventors: Andrew John Boeckl, Tarpon Springs, FL (US); David Edward Cookson, Orlando, FL (US)

(73) Assignee: FLURRY POWDERS, LLC, Tarpon Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/432,200

(22) Filed: Jun. 5, 2019

(65) Prior Publication Data
US 2019/0282502 A1    Sep. 19, 2019

Related U.S. Application Data

(63) Continuation-in-part of application No. 15/411,753, filed on Jan. 20, 2017, now Pat. No. 10,328,216.
(Continued)

(51) Int. Cl.
*A61K 9/16*     (2006.01)
*A61K 31/352*   (2006.01)
(Continued)

(52) U.S. Cl.
CPC .......... *A61K 9/1694* (2013.01); *A61K 9/0075* (2013.01); *A61K 9/1617* (2013.01);
(Continued)

(58) Field of Classification Search
None
See application file for complete search history.

(56) References Cited

U.S. PATENT DOCUMENTS

| 4,105,027 A | 8/1978 | Lundquist |
| 4,192,309 A | 3/1980 | Poulsen |

(Continued)

FOREIGN PATENT DOCUMENTS

| JP | 11-503731 T2 | 3/1999 |
| JP | 2002-507976 A | 3/2002 |

(Continued)

OTHER PUBLICATIONS

U.S. Appl. No. 15/411,753 , "Final Office Action", dated Oct. 22, 2018, 21 pages.
(Continued)

*Primary Examiner* — Kyung S Chang
(74) *Attorney, Agent, or Firm* — Kilpatrick Townsend & Stockton LLP

(57) ABSTRACT

A method of manufacturing a flowable and dispersible powder includes solubilizing a lipophilic substance in a terpene to form a mixture and treating the mixture to form a nanoemulsion dispersed in an aqueous solution. The aqueous solution includes at least one functional excipient. The nanoemulsion is then spray dried, thereby evaporating first the aqueous portion and then the terpene to form a dry powder formed from solid particles comprising the lipophilic substance.

14 Claims, 8 Drawing Sheets

Related U.S. Application Data

(60) Provisional application No. 62/280,968, filed on Jan. 20, 2016.

(51) Int. Cl.
 A61K 9/00 (2006.01)
 A61K 31/05 (2006.01)
 A61K 36/00 (2006.01)

(52) U.S. Cl.
 CPC ............ *A61K 9/1652* (2013.01); *A61K 31/05* (2013.01); *A61K 31/352* (2013.01); *A61K 36/00* (2013.01)

(56) References Cited

U.S. PATENT DOCUMENTS

| | | | |
|---|---|---|---|
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,192,528 A | 3/1993 | Radhakrishnan et al. | |
| 6,372,258 B1 | 4/2002 | Platz et al. | |
| 6,383,513 B1 | 5/2002 | Watts et al. | |
| 6,592,904 B2 | 7/2003 | Platz et al. | |
| 7,097,827 B2 | 8/2006 | Platz et al. | |
| 7,252,840 B1 | 8/2007 | Batycky et al. | |
| 9,132,246 B2 | 9/2015 | Gumaste et al. | |
| 10,328,216 B2 | 6/2019 | Boeckl et al. | |
| 2009/0291095 A1* | 11/2009 | Baker, Jr. ............. | A61K 39/292 424/184.1 |
| 2012/0141585 A1* | 6/2012 | Coulter ................ | A61K 9/1652 424/464 |
| 2013/0010259 A1 | 1/2013 | Carnevale | |
| 2013/0102591 A1 | 4/2013 | Salzman et al. | |
| 2016/0278973 A1 | 9/2016 | Chen et al. | |
| 2016/0279073 A1 | 9/2016 | Donsky et al. | |
| 2017/0072069 A1 | 3/2017 | Le et al. | |
| 2017/0232210 A1 | 8/2017 | Lemson | |
| 2019/0282502 A1 | 9/2019 | Boeckl et al. | |

FOREIGN PATENT DOCUMENTS

| | | |
|---|---|---|
| JP | 2003-507412 T2 | 2/2003 |
| JP | 2005-521710 T2 | 7/2005 |
| JP | 2013-518097 T2 | 5/2013 |
| WO | 9116038 | 10/1991 |
| WO | 2015068052 | 5/2015 |
| WO | 2015/127315 A1 | 8/2015 |
| WO | 2016/205923 A1 | 12/2016 |
| WO | 2017127641 | 7/2017 |

OTHER PUBLICATIONS

U.S. Appl. No. 15/411,753 , "Non-Final Office Action", dated Jun. 15, 2018, 17 pages.
U.S. Appl. No. 15/411,753 , "Notice of Allowance", dated Feb. 14, 2019, 10 pages.
U.S. Appl. No. 15/411,753 , "Restriction Requirement", dated Mar. 8, 2018, 13 pages.
Elsohly , "Marijuana and the Cannabiniods", Humana Press, Inc, Available online at : http://www.calgarycmmc.com/Ebooks%20%20i%20j%20k%20l%20m%20n%20o/Mahmoud%20A.%20ElSohly%20-%20Marijuana%20and%20the%20Cannabinoids.pdf, 333 pages.
EP17741989.2 , "Extended European Search Report", dated Aug. 23, 2019, 7 pages.
Gupta et al., "Formulation Strategies to Improve the Bioavailability of Poorly Absorbed Drugs with Special Emphasis on Self-Emulsifying Systems", Available online at: http://dx.doi.org/10.1155/2013/848043, Nov. 13, 2013, 16 pages.
Jafari et al., "Nano-Emulsion Production by Sonication and Microfluidization—A Comparison", International Journal of Food Properties, vol. 9, No. 3, 2006, pp. 475-485.
PCT/US2017/014279 , "International Preliminary Report on Patentability", dated Aug. 2, 2018, 9 pages.
PCT/US2017/014279 , "International Search Report and Written Opinion", dated Mar. 30, 2017, 12 pages.
'Discovery and development of statins', Wikipedia, May 2001 [retrieved from the internet on Aug. 21, 2020 at https://en.wikipedia.org/wiki/Discovery_and_development_of_statins p. 4 para 1.
'Granulation', Wikipedia, 2015 [retrieved from the internet on Aug. 24, 2020 at https://en.wikipedia.org/wiki/Granulation p. 1 para 2.
International Search Report and Written Opinion for PCT/US2020/036130 dated Sep. 9, 2020, all pages.
Examination report No. 1 for standard patent application No. AU 2017210319 dated Dec. 15, 2021, 4 pages.
Office Action for Israeli Patent Appln No. 260509 dated Oct. 31, 2021, all pages.
International Preliminary Report on Patentability for PCT/US2020/036130 dated Dec. 7, 2021, all pages.
Gallarate et al., "Formulation of Dry Emulsion for Topical Application" Journal of Dispersion Science and Technology 2009, 30:823-833.
Geller et al., "Development of an Inhaled Dry-Powder Formulation of Tobramycin Using PulmoSphere Technology," Journal of Aerosol Medicine and Pulmonary Drug Delivery 2011, 24(4):175-182.
Official Action with art cited from the Israel Patent Office dated Aug. 16, 2022 for No. 260509, all pages. This office action is in Hebrew. Applicant is not in possession of an English translation.
Official Action from the Canadian Patent Office dated Jan. 25, 2023 for No. 3,011,185, all pages.
Office Action dated Sep. 28, 2023 for Israel Application No. 260509, all pages.

\* cited by examiner

302 — MIX AN OIL SOLUTION WITH A WATER SOLUTION TO FORM AN OIL-IN-WATER EMULSION COMPOSITION

304 — SPRAY DRY THE OIL-IN-WATER EMULSION TO FORM A DRY POWDER COMPOSITION

ENCAPSULATION OF LIPOPHILIC INGREDIENTS IN DISPERSIBLE SPRAY DRIED POWDERS SUITABLE FOR INHALATION

CROSS-REFERENCE TO RELATED APPLICATIONS

This application is a continuation-in-part of U.S. Non-Provisional application No. 15/411,753, filed on Jan. 20, 2017, which is a non-provisional of U.S. Provisional Application No. 62/280,968, filed on Jan. 20, 2016, the complete disclosures of which are herein incorporated by reference.

BACKGROUND OF THE INVENTION

Due to their hydrophobic nature and low solubility in water, lipophilic active substances often exhibit poor bioavailability via the oral gastrointestinal (GI) delivery route. Furthermore, accurate and precise dosing is poor for drugs delivered via the GI system due to inherent variability caused by factors such as fasting state and first pass metabolism. As an alternative, pulmonary delivery using a dry powder inhaler (DPI) may be used. Traditional lactose-carrier (lactose blend) formulations for DPIs typically offer low drug loads, commonly less than 6% (wt/wt), and low delivery efficiencies (DE), typically delivering <30% of the drug to the lungs. Lactose blends are also highly flow rate dependent, showing significant variability with respect to aerodynamic performance. Once formulated, lactose blends rely on inter-particle forces to bind micronized drug to larger lactose carrier particles to maintain a uniform distribution of drug. This can present challenges during transportation and filling of powder into packages, which impart mechanical energy capable of redistributing or otherwise disturbing blend uniformity.

Engineered particles (e.g. spray dried) for DPIs offer significant improvements in drug payload, DE, good aerosol performance across a wide flow rates, and a lower risk for segregation of drug from excipients. However, lipophilic drug substances are challenging to encapsulate into dry, flowable, and dispersible powders that are compatible with dry powder inhalers. In addition, oils and fats exhibit poor dissolution and dispersion when incorporated into aqueous systems which are common in the preparation of annex solutions used to produce spray dried powders. This invention relates to new uses for terpenes as non-toxic, natural solubilizers for preparing vehicles (or annex solutions) which may then be spray dried to produce powders comprising various drugs, agricultural chemicals, cosmetics, and foods.

BRIEF SUMMARY OF THE INVENTION

The present disclosure generally relates to dry powder compositions and methods for administering and preparing such compositions. Embodiments are directed to dry powder compositions in which volatile terpenes are used as processing aids to create nanoemulsions containing lipophilic active substances and/or slightly soluble to practically insoluble substances, which may then be stabilized in dry powder form, and to methods for preparing and using such compounds. Slightly soluble substances are defined as one part solute in 100-1000 ml of solvent and practically insoluble substances are defined as one part solute in greater than 10,000 ml solvent. One group of such lipophilic active substances and/or insoluble or slightly soluble substance are extracts of cannabis, which are commercially available as sticky, resinous oils, or as high purity crystalline forms. The dry powder compositions may include any suitable lipophilic substances and/or insoluble or slightly soluble substance. For example, there may be an oil-in-water nanoemulsion composition that includes cannabinoids in the oil fraction that is spray dried to form a dry powder composition. The oil-in-water emulsion compositions may include a hydrophobic amino acid, e.g. leucine, a disaccharide, e.g. trehalose, and/or an oligosaccharide, e.g. inulin. Such dry powder compositions may be administered to a subject via pulmonary inhalation.

In one aspect, a method of manufacturing a flowable and dispersible powder is provided. The method may include solubilizing a lipophilic substance in a terpene to form a mixture and treating the mixture to form a nanoemulsion dispersed in an aqueous solution. In other embodiments, an insoluble or slightly soluble substance may be mixed into a terpene to form a suspension, which may be dispersed into an aqueous solution. The aqueous solution may include at least one functional excipient. The terpene fraction may include at least one functional excipient. The method may also include spraying drying the nanoemulsion, thereby evaporating at least a portion of the terpene and the majority of the water to form a suitable dry powder formed from solid particles that include the lipophilic and/or insoluble or slightly soluble substance.

In another aspect, a method of manufacturing a flowable and dispersible powder includes dissolving a lipophilic ingredient in an organic solvent to form a lipophilic phase and dissolving at least one of a surfactant or an emulsifier in the lipophilic phase. The method may also include dissolving one or more excipients into water to form an aqueous phase and chilling the aqueous phase to between about 1° C. and 10° C. The method may further include dispersing the lipophilic phase into the chilled aqueous phase to form an emulsion that includes nanosized oil droplets. Alternatively, the emulsion may be prepared by heating the organic and aqueous phases to between 50 and 75° C. The method may include spray drying the emulsion to form a dry powder that includes one or more lipophilic ingredients.

In another aspect, a method of manufacturing a flowable and dispersible powder may include mixing an oil solution with a water solution to form an oil-in-water emulsion composition. The oil solution may include a cannabinoid. The method may also include spray drying the oil-in-water emulsion composition to form a dry powder composition.

In another aspect, a dry powder composition is provided. The dry powder composition may include a lipophilic component and one or more of a hydrophobic amino acid, a disaccharide, an oligosaccharide, a surfactant, an emulsifier, a stabilizing additive, or a bulking agent. The dry powder composition may have bulk density between 0.05 and 0.30 g/cm$^3$, tap density between 0.10 and 0.60 g/cm$^3$, and moisture content below about 10% w/w. The dry powder composition may also include between about 0.01% and 60% w/w of the lipophilic component.

In another aspect, a method of aerosolizing a dry powder formulation is provided. The method may include providing a dry powder formulation that has a lipophilic component and one or more of a hydrophobic amino acid, a disaccharide, an oligosaccharide, a surfactant, an emulsifier, a stabilizing additive, or a bulking agent. The dry powder composition may include between about 0.01% and 50% w/w of the lipophilic component. The method may also include introducing the dry powder formulation to an aerosolization device and introducing the dry powder formulation to a gas stream within the aerosolization device to disperse the dry powder formulation.

The features and advantages of the present invention will be apparent to those skilled in the art. While numerous changes may be made by those skilled in the art, such changes are within the spirit of the invention.

BRIEF DESCRIPTION OF THE DRAWINGS

FIG. 3 is a flowchart depicting a process for manufacturing a flowable and dispersible powder according to embodiments.

DETAILED DESCRIPTION OF THE INVENTION

Figure 1:
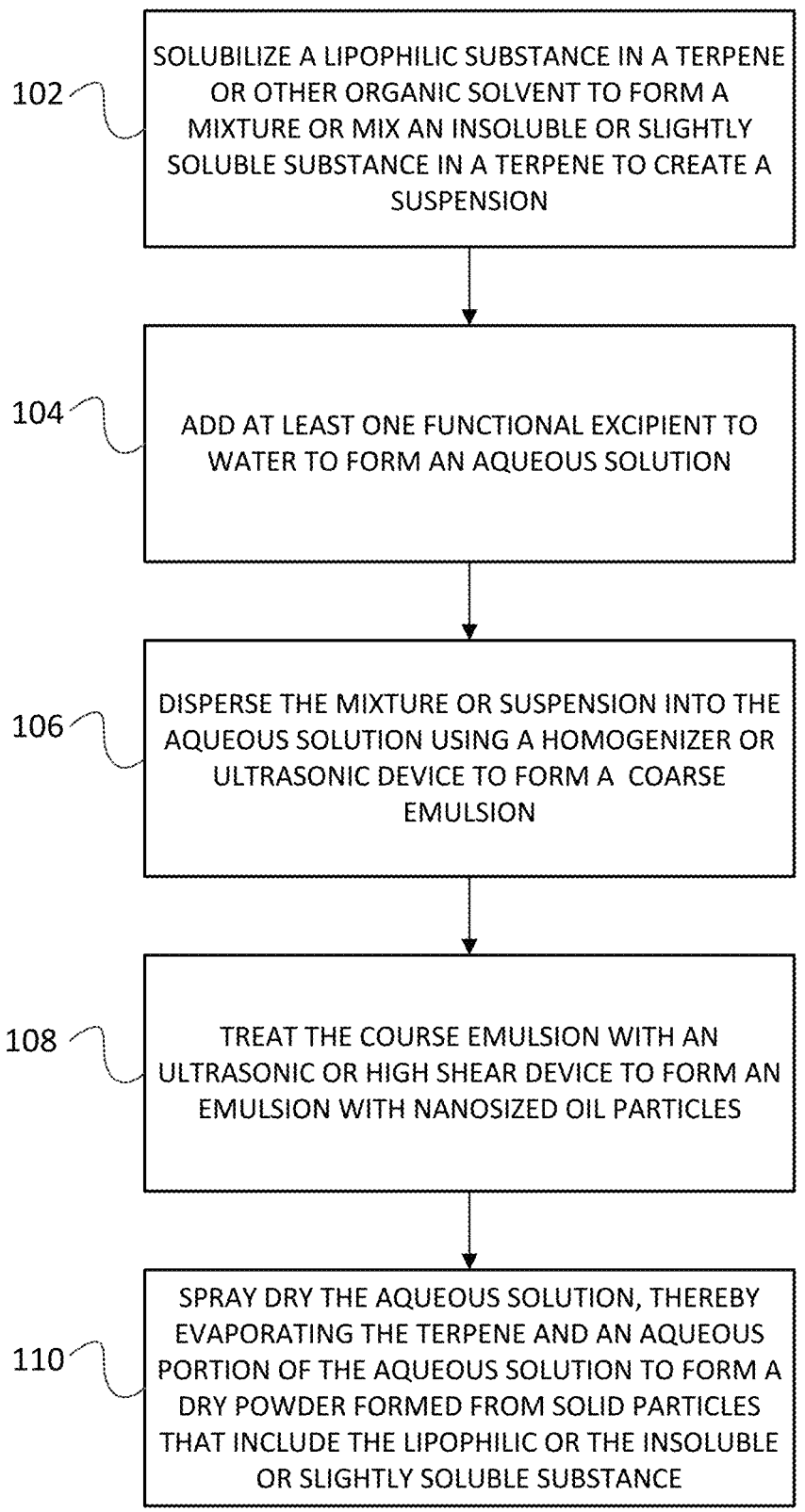
FIG. 1 is a flowchart depicting a process for manufacturing a flowable and dispersible powder according to embodiments.
Figure 2:
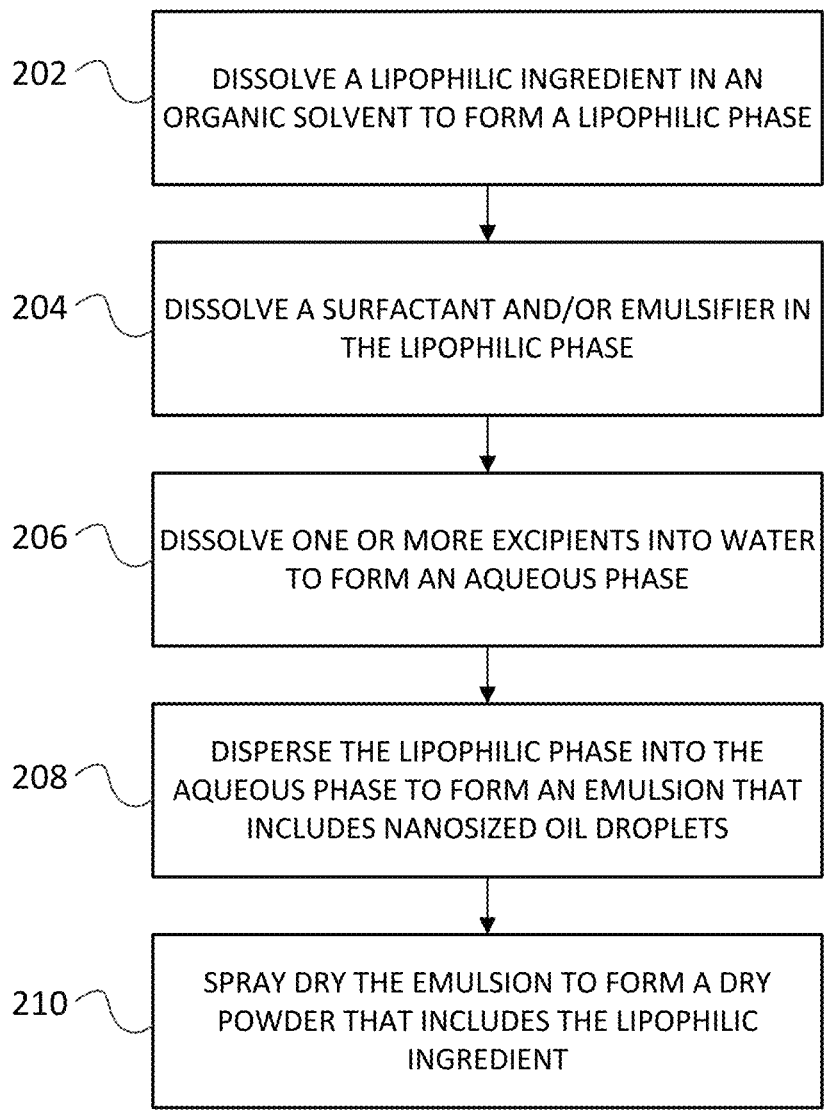
FIG. 2 is a flowchart depicting a process for manufacturing a flowable and dispersible powder according to embodiments.

Embodiments of the present invention relate to dry powder compositions for improved pulmonary, topical, enteral, or parenteral delivery of lipophilic substances and/or insoluble or slightly soluble substances, and to methods for the preparation and use of such compositions. More particularly, volatile terpenes are employed as processing aids to achieve dispersion of the lipophilic fraction(s) in a nanoemulsion which is stabilized and encapsulated in functional excipients using a spray drying method. For example, the terpenes may be employed to serve as a protective processing intermediate during a drying process to prevent hydrolysis of the insoluble or slightly soluble substance (which may include a lipophilic substance). Hydrolysis is one of the primary chemical reactions that affect the stability of a drug. Hydrolysis is the reaction of a molecule with water resulting in the cleavage of a chemical bond within that molecule. Though there exist many functional groups that can undergo hydrolysis, esters, lactones, amides, lactams, carbamates, imides, and imines are the most common ones found in drugs.

Once manufactured, drugs that are sensitive to hydrolysis are typically packaged under environmental conditions and in configurations designed to protect against exposure to water. For many of these drugs, process intermediates and processing steps used during manufacturing are also developed to limit exposure to water. In the case of processing into powders via spray drying or granulation, where a liquid carrier (annex solution) is required to dissolve or suspend the formulation so that it can be atomized, this usually involves the use of organic solvents which require closed loop spray drying systems, which add cost and complexity to manufacturing.

The invention contemplated herein enables aqueous based spray drying or granulation of drug substances that are sensitive to hydrolysis. This system relies on the use of terpenes, whose primary function is to protect the drug substance from hydrolysis during preparation and storage of an aqueous based annex solution suitable for spray drying. The invention describes a formulation approach whereby the drug is introduced into a terpene along with surfactant. Using an ultrasonic or high shear device, this terpene mixture is then dispersed into to an aqueous mixture that contains select functional excipients to form an oil-in-water emulsion. Encapsulation of the drug in the dispersed terpene phase, protects it from hydrolysis during formulation and storage until spray drying. The oil-in-water emulsion is the annex solution that is atomized, or sprayed, during powder production.

In some embodiments, the drug substance is solubilized into the terpene during formulation of the annex solution. In other embodiments, the drug substance is a solid suspended in the terpene during formulation of the annex solution.

During the drying step, annex solution is atomized into droplets which then dry into solid particles. In the first stage of particle formation, water evaporates from the droplets which undergo evaporative cooling, maintaining a relatively low temperature relative to that within the drying chamber. Water has roughly 11 times higher vapor pressure relative to d-limonene, therefore it would be driven off first during drying. Once a substantial quantity of water has evaporated, then the terpene fraction is volatilized. By evaporating substantially all the water first, the drug substance is protected by the terpene during drying. At the conclusion of the drying process, substantially all the water and terpene are evaporated, forming a dry powder from solid particles comprising the drug substance. Table 1 illustrates vapor pressures and boiling points of water and d-Limonene.

TABLE 1

| Vapor pressures and boiling points: | | | |
|---|---|---|---|
| Component | Boiling Point (° C.) | Vapor Pressure at 25° C. (mm Hg) | Vapor Pressure at 53.8° C. (mm Hg) |
| d-Limonene | 177 | 2.0 | 10 |
| Water | 100 | 23.8 | 111.4 |

Treatment with nano-sized units of lipophilic drug substances has shown enhanced bioavailability in vivo, as described in T. Yi, J. Wan, H. Xu, X. Yang. A new solid self-microemulsifying formulation prepared by spray-drying to improve the oral bioavailability of poorly water soluble drugs. European Journal of Pharmaceutics and Biopharmaceutics, Volume 70, Issue 2, October 2008, Pages 439-444 and in S. Gupta, R. Kesarla, A. Omri. Formulation Strategies to Improve the Bioavailability of Poorly Absorbed Drugs with Special Emphasis on Self-Emulsifying Systems. ISRN Pharmaceutics, December 2013, the entire contents of which are hereby incorporated by reference. The increase in surface area to volume with decreasing particle size results in greater potential for efficient transport and uptake in the human body. Such lipophilic dry powder compositions may be administered to a subject via pulmonary inhalation in an amount effective to treat and/or prevent a number of conditions, such as systemic and/or lung conditions.

An inhalable dry powder preparation for lipophilic drug substances offers advantages over oral GI delivery. For example, pulmonary delivery offers a high surface area with rapid absorption due to high vascularization and circumvention of the first pass effect, as described in Sung, J. C.; Pulliam, B. L.; Edwards, D. A. Nanoparticles for drug delivery to the lungs. Trends in Biotechnology. 2007, 25, 563-570, the entire contents of which is hereby incorporated by reference. Rapid drug absorption may be favorable in analgesic, antiemetic, and other medicaments. Further, powder compositions may be engineered such that a controlled fraction of the dose impacts the deep lung (fine particle fraction) while the remainder impacts mucosa in the upper airways. Such a delivery method results in rapid uptake via the lung followed by a slow, sustained release of drug via GI and transmucosal modes. By these means, pharmacokinetics of the product may be modulated.

A formulation and a spray drying technique are used to stabilize lipophilic active ingredients in a dry powder having good flow properties and dispersibility. The lipophilic ingredients are solubilized and/or diluted in carrier terpene(s) and the combined mixture is treated to form a nanoemulsion dispersed in an aqueous solution. The aqueous fraction contains dissolved functional excipients which serve as bulking, encapsulation, stabilizing, and flow enhancement agents. During the spray drying process the aqueous and terpene carrier phases evaporate to form solid particles. The resulting powders exhibit excellent dispersibility into aerosol suitable for pulmonary delivery. Dissolution of powders into aqueous liquids produces a nano-sized dispersion of the oil phase. Such methods have proven to be very efficient, stable, and exhibit excellent batch to batch consistency.

In some embodiments, a free flowing powder may be created and/or further processed using a wet granulation device. For example, a previously spray dried cannabinoid powder, such as those described above, may be charged into a chamber of a granulator. An aqueous binding agent can be either pumped into the contents of the chamber in a high shear type granulator or can be sprayed onto the powder in a fluidized bed granulator. In the case of high shear granulation, the granulated powder would be dried in a subsequent step. In fluidized bed granulation, drying occurs concurrently with spray coating and fluidization; the drying process is regulated by control of spraying feed rate, drying gas flow rate, and drying gas temperature.

In some embodiments, a free flowing powder may be created using a high shear or fluidized bed granulator whereby the powder charged into the granulation chamber is comprised of a previously spray dried cannabinoid powder and the coating and binding agent is comprised of a cannabinoid oil-in-water emulsion having binders and other functional excipients.

In some embodiments, a free flowing powder may be created using a high shear or fluidized bed granulator whereby the powder charged into the granulation chamber is comprised of a non-active powder such as lactose, mannitol, having a mean geometric diameter between 50 and 1000 μm. The coating and binding agent may be comprised of a cannabinoid oil-in-water emulsion having binders and other functional excipients.

In some embodiments, coated products may be created using a high shear or fluidized bed granulator whereby a food, supplement, tea, coffee, or other solid product is charged into the granulation chamber. The coating agent may include a cannabinoid oil-in-water emulsion having binders and other functional excipients.

Lipophilic ingredients, such as cannabinoid extracts, are commonly available as sticky, viscous concentrates which present processing challenges for discretization into more desirable nano-sized particles. Dissolving these challenging drug substances in solvents reduces surface tension and enables their break-up into nano-sized droplets via high shear mechanisms such as ultrasonics or microfluidizers. The inclusion of surfactant in the oil phase stabilizes nano-sized droplets in an emulsion by acting as a barrier against droplet coalescence, thereby enhancing emulsion stability. Formulating with excipients having low aqueous solubility (e.g. leucine), the nano-sized sticky oil phase is encapsulated within a shell which precipitates first during the drying event. This entrapment produces particles having surface characteristics which are dominated by the encapsulating excipient. Use of leucine as an encapsulating excipient has been shown to impart excellent flowability and dispersibility to powders. Cannabinoids are a class of compounds derived from Cannabis plants. At least 113 cannabinoids have been identified in the plant, as described in O. Aizpurua-Olaizola, U. Soydaner, E. ÖztUrk, et al. Evolution of the Cannabinoid and Terpene Content during the Growth of Cannabis sativa Plants from Different Chemotypes. J. Nat. Prod., 2016, 79 (2), pp 324-331, the entire contents of which is hereby incorporated by reference. The two primary cannabinoids contained in Cannabis are Δ9-tetrahydrocannabinol (THC):

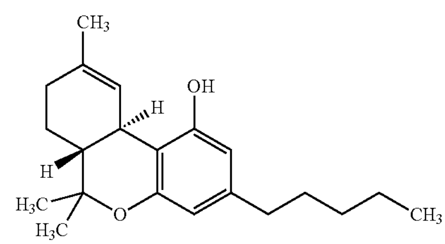 [SMILES: CCCCCc1cc(O)c2c(c1)OC(C)(C)[C@@H]1CCC(C)=C[C@@H]21]

and cannabidiol (CBD):

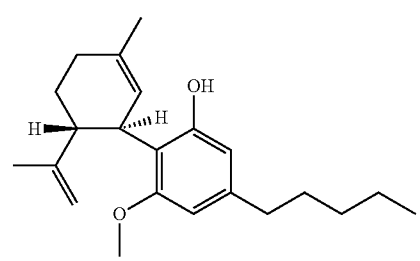 [SMILES: C=C(C)[C@@H]1CCC(C)=C[C@H]1c1c(O)cc(CCCCC)cc1OC]

Commonly used recreationally, cannabinoids are being used and studied for use in a number of medical conditions including, but not limited to, epilepsy, refractory epilepsy, fragile X syndrome, osteoarthritis, anxiety, chronic pain. Other medical uses may include the treatment of disorders including insomnia, fibromyalgia, spinal injury, phantom limbs, migraines and/or other headaches, cramps, sleep apnea, cancer, muscular dystrophy, HIV/AIDS, glaucoma, hypertension, fatigue, asthma, ALS, lack of appetite, anorexia, cachexia, gastrointestinal disorders, nausea, diabetes, Crohn's, anxiety, ADD/ADHD, stress, bipolar disorder, obsessive compulsive disorder (OCD), post-traumatic stress disorder (PTSD), depression, Tourette's, seizures (including Dravet Syndrome), multiple sclerosis, Alzheimer's, Parkinson's, spasticity, osteoporosis, inflammation, arthritis, sexual performance and libido enhancement, and/or symptoms thereof.

Cannabinoids are commonly administered in smoked, vaped, edible, and topical forms. Once in the bloodstream, certain cannabinoids are metabolized into compounds that may be of clinical or therapeutic interest. Δ9THC (delta 9-tetrahydrocannabinol), for example, is metabolized into 11-hydroxy-Δ9THC (11-OH-THC), which is further metabolized into 11-nor-9-carboxy-Δ9-tetrahydrocannbinol (THC—COOH). 11-hydroxy-Δ9THC (11-OH-THC), the primary metabolite of Δ9THC, has been shown to be more psychoactive than Δ9THC and more rapidly crosses the blood-brain barrier, indicated greater pharmacological activity of the metabolite as disclosed in Lemberger L, Crabtree R E, Rowe H M. 11-hydroxy- 9 -tetrahydrocannabinol: pharmacology, disposition, and metabolism of a major metabolite of marihuana in man. Science. 1972 Jul. 7; 177(4043):62-4, the entire contents of which is hereby incorporated by reference. THC—COOH, the secondary metabolite, is excreted in urine and the target in testing methods developed for the detection of cannabis use. Similarly, delta 8-tetrahydrocannabinol (delta 8-THC), is metabolized into 11-hydroxy-delta 8-THC (11-OH-delta 8-THC), and then 11-oxo-delta 8-THC.

Currently, cannabinoid metabolites are formed within the human body following enteral administration and by inhalation of smoked or vaped cannabis preparations. Due to high variability in metabolic function between humans and the influence of lifestyle and environmental conditions, one can assume that there would be high variability in both the quantity and the rate of formation of metabolites.

A dry powder inhaler (DPI) preparation formulated to deliver synthetic 11-OH-THC may be faster acting and require less active ingredient to achieve the same therapeutic effect as a larger dose of THC. Furthermore, the fixed dose of a DPI enables control over the dose and pulmonary delivery should ensure consistent pharmacokinetics; aspects that are poorly controlled during metabolism in vivo.

Cannabinoid containing drug substances that have been refined by distillation or other fractionation processes are challenging to formulate with because of their physical and chemical attributes. Having low solubility and high permeability, cannabinoids are designated as BCS (Biopharmaceutics Classification System) Class II drugs. Cannabinoid distillates and concentrates are commonly found in the form of viscous and sticky oils, though certain cannabinoids can be further refined into high purity crystalline forms. Due to these attributes, manufacturing dosage forms containing accurate and precise doses of active ingredients can be challenging. The central issue is ensuring homogenous dispersion while mixing or blending drug substance(s) with the other functional ingredients (e.g. fillers, flavonoids, binders, disintegrants, lubricants).

The invention contemplated herein produces a free flowing and homogenous cannabinoid powder or coated product. The process employs an oil in water emulsion as a precursor to powder production. During the preparation of this emulsion, select cannabinoids are dissolved in the terpene component. Functional excipients including are solubilized in the aqueous component. A coarse emulsion is formed when aqueous and terpene-cannabinoid components are combined in a vessel under mechanical agitation. This coarse emulsion is then processed through a high shear device, such as a microfluidizer, to form a fine emulsion.

Administration of an effective amount of a cannabinoid composition, including tetrahydrocannabinol (THC), tetrahydrocannabinolic acid (THCa), cannabidiol (CBD), cannabidiolic acid (CBDa), cannabinol (CBN), cannabichromene (CBC), cannabigerol (CBG) and others, of the present disclosure may be particularly useful in treating conditions including, but not limited to pain, anxiety, sexual performance, and insomnia.

While largely discussed in relation to cannabinoid compositions, it will be appreciated that compositions containing other lipophilic drug substances may be manufactured and/or administered using the methods described herein. Examples of other lipophilic/low solubility drug substances include, but are not limited to, those shown in Table 2 below.

TABLE 2

Lipophilic/low solubility drug substances

| Drug | Solubility (ug/ml) | Class |
|---|---|---|
| Alpha tocopherol | 0.007 | tocopherol |
| Amphotericin B | 82 | aminoglycoside |
| Atorvastatin | 0.5 | statin |
| Azithromycin | 514 | azalide (macrolide antibiotic) |
| Beclomethasone | 2.1 | glucocorticoid |
| Budesonide | 46 | glucocorticoid |
| Caspofungin | 367 | echinocandin |
| Ciprofloxacin | 1350 | fluoroquinoline |
| Clemastine | 0.4 | antihistamine |
| Clofazimine | 1.5 | leprostatic |
| Cyclosporine | 5 | immunosuppressant |
| Dihydroergotamine | 229 | ergot alkaloid |
| Dronabinol | 2.6 | cannabinoid |
| Dutasteride | 0.9 | 5alpha reductase inhibitors |
| Erithromycin | 459 | macrolide antibiotic |
| Felodipine | 7.1 | calcium channel blocker |
| Fentanyl | 24 | opiate |
| Flecainide | 32 | sodium channel blocker |
| Fluticasone furoate | 43.4 | glucocorticoid |
| Fluticasone proprionate | 11.4 | glucocorticoid |
| Furosemide | 118 | loop diuretic |
| Glycopyrronium | 0.95 | LAMA |
| Indacaterol | 8 | LABA |
| Itraconazole | 9.6 | triazole |
| Loxapine | 103 | tricyclic antipsychotic |
| Mometasone | 5.2 | glucocorticoid |
| Nimodipine | 12 | calcium channel blocker |
| Tacrolimus | 4 | macrolide immunosuppressant |
| Tretinoin | 4.8 | retinoid |
| Vilanterol | 11.8 | LABA |

In one embodiment, a composition of the present disclosure is a dry powder that includes cannabinoids. As used herein, the term cannabinoids includes natural derivatives of cannabis or hemp plant, or synthesized analogues. As used herein, the term "dry" means that the composition has a moisture content such that micron-size particles are readily dispersible in an inhalation device to form an aerosol, while larger particles exhibit good flow properties. In some embodiments, this moisture content may be below about 10% by weight water, below about 7% by weight water, below about 5% by weight water or below about 3% by weight water. Furthermore, as used herein, the term "inhalation powder" means a composition that includes finely dispersed solid particles that are capable of being readily dispersed in an inhalation device and subsequently inhaled by a subject so that the particles reach the lungs to permit penetration into the upper and lower airways. Thus, the powder is said to be "respirable." In some embodiments, a dry powder composition of the present disclosure may have a tap density greater than about 0.1 g/cm$^3$, greater than about 0.20 g/cm$^3$ or greater than about 0.4 g/cm$^3$ and mass median aerodynamic diameter (MMAD) between 1 and 4 um. While cannabinoids may be predominately used in the descriptions contained in this disclosure, it should be understood that the present disclosure may be practiced with any other substantially lipophilic active and low solubility drug substances (such as those disclosed in Table 1 above), and derivatives and analogues thereof, among other things, to treat various respiratory and systemic conditions.

nary delivery via DPI approach include rapid absorption similar to smoking or vaporizing but without the health risks associated with these traditional forms of inhaled delivery. Additional advantages include DE's greater than 60% and high dose precision. Aerodynamic properties of a number of powder batches according to the present invention are shown in Tables 3 and 4 below.

TABLE 3

Mean values (n = 3) for physical and aerodynamic properties (Anderson Cascade Impactor and Plastiape RS01 inhaler) of select powder batches containing oily extracts [GSD—geometric standard deviation; FPF—fine particle fraction (powder mass recovered on plates 2 to 7 + powder mass recovered on filter)/(mass emitted from capsule − residual powder mass on inhaler)]

| Batch Id | Oil Extract (% wt/wt) | Bulk Density (g/mm³) | Tap Density (g/mm³) | $D_{50}$ (um) | MMAD (um) | GSD | ED (%) | FPF (%) | DE (%) |
|---|---|---|---|---|---|---|---|---|---|
| P20150828-2 | 6.4 | 0.12 | x | 2.1 | 3.4 | 1.5 | 82 | 82 | 67 |
| P20150828-3 | 6.4 | 0.13 | x | 1.9 | 2.9 | 1.8 | 78 | 93 | 72 |
| P20170105-1 | 7.5 | 0.12 | x | 2.2 | 2.8 | 1.6 | 90 | 95 | 85 |
| P20170105-2 | 6.6 | 0.20 | x | 2.0 | 3.3 | 1.6 | 86 | 85 | 73 |
| P20161222-7 | 7.4 | 0.12 | x | 2.2 | 2.7 | 1.8 | 88 | 88 | 78 |
| P20160611-1 | 12.0 | 0.06 | 0.11 | 1.9 | 2.4 | 1.9 | 95 | 85 | 81 |
| P20160611-3 | 12.3 | 0.06 | 0.12 | 2.2 | 2.3 | 2.1 | 97 | 93 | 90 |
| P20160611-7 | 18.4 | 0.09 | 0.16 | 2.6 | 3.5 | 2.0 | 99 | 64 | 64 |

In certain specific embodiments, a dry powder composition of the present disclosure comprises cannabinoids present in an amount of between about 1% and 60%, in some cases between about 1% and 20% and in other cases between about 21% and 60%, in some cases between about 4% and 15%, and still in other cases about 12% by weight of the composition, the powder having a tap density between about 0.1 g/cm³ and 0.3 g/cm³. The dry powder compositions may further include leucine in an amount of between about 10% and 90%, trehalose or inulin of between about 1% and 60%, and surfactant of between about 0.1% and 10% by weight of the composition. In some cases, the dry powder compositions may further include leucine in an amount of between about 40% and 70%, trehalose or inulin of between about 20% and 50%, surfactant of between about 0.1% and 5% by weight of the composition. In still other cases, the dry powder compositions may further include leucine in an amount of about 60%, trehalose or inulin in the amount of about 20%, surfactant in the amount of about 1.5% by weight of the composition. In some embodiments, particles of a dry powder composition may have an average particle size of less than or equal to about 10 micrometers (um) in diameter as defined by the MMAD. In some embodiments, at least 95% of the particles have a MMAD of less than about 10 µm. In some embodiments, the diameter may be less than or equal to about 7 µm. In other embodiments, the diameter may be less than or equal to about 5 µm. In certain specific embodiments, the diameter may be between about 0.5 µm and about 5 µm in diameter, particularly between about 1 µm to about 3 µm. Dry powder compositions of the present disclosure that include particles having an average particle size of less than or equal to about 5 µm in diameter may be particularly useful for delivery via an oral inhalation device. In the case of cannabinoids, advantages of pulmo-

TABLE 4

Mean values (n = 3) for aerodynamic properties (Anderson Cascade Impactor and Plastiape RS01 inhaler) of batch P20161222-7 tested at two standard flow rates.

| Flow Rate (lpm) | MMAD (um) | GSD | ED (%) | FPF (%) | DE (%) |
|---|---|---|---|---|---|
| 28.3 | 3.43 | 1.45 | 82 | 82 | 67 |
| 60 | 2.92 | 1.77 | 78 | 93 | 72 |

In other embodiments, a dry powder composition of the present disclosure may comprise particles having an average particle size of greater than or equal to about 10 µm in diameter as defined by IVIMAD (measured using cascade impaction). In some embodiments, at least 95% of the particles have a IVIMAD of greater than about 10 µm. In certain specific embodiments, the particle size may be between about 10 µm and about 50 µm in diameter, particularly about 20 µm to about 40 µm. Dry powder compositions of the present disclosure that include particles having an average particle size of greater than or equal to about 10 µm in diameter may be particularly useful for nasal delivery or for oral solid dosage forms, or as preparations intended to enhance stability of the active component.

In other embodiments, a dry powder composition may include particles having a broader range, having approximately 90% of the particles between 1 to about 12 µm. This range of particle sizes may be useful for simultaneous delivery of actives to the lungs and upper airways via an oral inhalation device. For example, the finer particles impact the deep lung while the larger particles impact mucosa in the upper airways, resulting in rapid uptake via the lung followed by a slow, sustained release of drug via GI and transmucosal modes. Specifically, a control of size fractions present in a bimodal and/or broad monomodal distribution would allow for control over pharmacokinetic profile. Active lipophilic substances delivered to the lungs would be more rapidly absorbed into the bloodstream, while the fraction deposited on the upper airways would be absorbed more slowly, similar to the absorption of oral solid dosages. This could prospectively result in a fast-acting drug (short Tmax) with sustained drug activity (long half-life).

In some embodiments, the particles may be hollow. In some embodiments, the particles may be porous, having a sponge-like appearance. In some embodiments, the particles may have a spheroidal shape distribution, which may be relatively uniform. In other embodiments the particles are corrugated, appearing as wrinkled raisins. In cannabinoid embodiments, the potency as measured by select cannabinoid concentration is effectively unchanged when compared to the unformulated drug (i.e. within 10% of the unformulated drug).

Administration of an effective amount of a cannabinoid composition, including tetrahydrocannabinol (THC), tetrahydrocannabinolic acid (THCa), cannabidiol (CBD), cannabidiolic acid (CBDa), cannabinol (CBN), cannabichromene (CBC), cannabigerol (CBG) and others, of the present disclosure may be particularly useful in treating conditions including, but not limited to, pain, cancer, HIV, seizures, spasticity, multiple sclerosis, muscular dystrophy, Parkinson's, Tourette syndrome, Huntington's disease, Alzheimer's, glaucoma, anxiety, anorexia, cachexia, PTSD, OCD, inflammation, insomnia, arthritis, lupus, neurodegenerative diseases, and sexual performance disorders.

When heated during smoking or vaping, cannabinoid acids such as THCa and CBDa decarboxylate to form THC and CBD. Due to the relatively low temperatures employed in the spray drying process (i.e. <80° C.), production of powders containing cannabinoid acids (e.g. THCa, CBDa) of interest would be feasible.

In cannabinoid embodiments, suitable forms of lipophilic drug substances include oils, resins, and crystals which may be used to formulate dry powder products. These drug substances may be produced by any number of commercially available methods including solvent (e.g. butane, propane, hexane) and supercritical extraction (e.g. $CO_2$). The resultant drug substances may be comprised of 40-99.9% cannabinoids. Synthetic cannabinoids, such as the THC MARINOL® (dronabinol), may also be included.

In some embodiments, in addition to lipophilic drugs, a composition of the present disclosure may further include one or more additives. One example of a suitable additive is a hydrophobic amino acid. Such hydrophobic amino acids may include, but are not limited to, tryptophan, tyrosine, leucine, dileucine, trileucine and phenylalanine. In some embodiments, it may be desirable to include a hydrophobic amino acid in a lipophilic composition so as to improve the physical stability and/or dispersibility of the composition, to improve the chemical stability of cannabinoids and/or to alter the taste of the composition by masking the bitter taste of cannabinoids, and/or to alter the rate the composition is absorbed into the systemic circulation from the lung (e.g., increase or slow the rate of absorption). While not wishing to be bound to any particular theory, it is currently believed that the hydrophobic amino acid additive remains on the surface of the particles and protects them from moisture and light, thereby increasing the stability of the formulation.

Another suitable additive may be a cellulose based polymer and/or a polymeric agent used to modify surface properties. Such polymeric agents may include, but are not limited to, hyaluronic acid, polyethyleneglycol, hydroxypropylmethylcellulose (HPMC) and methylcellulose (MC). In some lipophilic dry powder embodiments, it may be desirable to include cellulose based polymers to improve the physical stability, powder handling, and/or dispersibility of the composition, to improve the chemical stability, and/or to alter the rate the composition is absorbed into the systemic circulation from the lung (e.g., increase or slow the rate). While not wishing to be bound to any particular theory, it is currently believed that the cellulose based polymer additive remains on the surface of the particles and protects them from moisture and light, thereby increasing the stability of the formulation.

Another example of a suitable additive is a carbohydrate bulking agent. Such carbohydrate bulking agents may include, but are not limited to, lactose, mannitol, trehalose, raffinose, and maltodextrins. In some embodiments, it may be desirable to include a carbohydrate bulking agent in a composition of the present disclosure so as to improve the physical stability of the composition. Furthermore, in some embodiments, the carbohydrate bulking agent may also improve the chemical stability of cannabinoids or lipophilic substances.

Another suitable additive is a volatile terpene. Such terpenes may include, but are not limited to, d-limonene, other grades of limonene, and beta-myrcene. Naturally occurring and refined cannabinoid substances may contain over 100 terpenes, as described in Turner C. E., M. A. Elsohly and E. G. Boeren, 1980. Constituents of Cannabis sativa L. XVII. A review of the natural constituents. Journal of Natural Products 43 (2): 169-234 and in R. Brenneisen, M. A ElSohly. Marijuana and the Cannabinoids, Chapter 2, p. 28, the entire contents of which are hereby incorporated by reference. In some embodiments, it may be desirable to include additional terpenes to aid in the processing of viscous lipophilic active substances into nanometer sized droplets dispersed in an aqueous phase prior to powder production via spray drying. The active lipophilic substance is dissolved into the terpene and then sequentially processed into nano/micrometer scale oil in water emulsions using homogenizers (e.g. Ultra-Turrax, IKA) or ultrasonic methods (e.g. Sonifier, Branson). Further refinement into nanometer scale ($D_{50}$ of 0.1 to 0.5 µm) oil-in-water emulsions is accomplished using ultrasonic (e.g. Sonifier, Branson) and/or high shear (e.g. M110Y, Microfluidics) equipment operated according to common practiced methods. In some embodiments, it may be desirable to incorporate surfactant (s) into the active oil/terpene mixture to stabilize emulsion droplet size during processing. While not wishing to be bound to any particular theory, it is currently believed that, like water, the terpenes are largely fugitive during the spray drying process and that residual added terpenes used for processing are minimal in the dried powder compositions. It will be apparent to experts in the field that the use of other fugitive or volatile elements is not restricted to terpenes and that other volatiles may be contemplated.

Surfactants and/or emulsifiers may be used to stabilize the active/solvent phase as an oil in water emulsion having nanometer sized droplets. Examples of stabilizing additives include non-ionic detergents, nonionic block copolymers, ionic surfactants, phospholipids (including DSPC), citrates (including sodium citrate and dylauryl citrate), polysorbates, sorbitan laurate, polyglyceryl-4 laurate, and cyclic oligosaccharides (e.g. alphadextrin and beta-cyclodextrin). Other additives known to those of ordinary skill in the art may also be included.

Generally, additives suitable for use in the compositions of the present disclosure may be included in an amount of about 99% or less by weight of the dry powder composition, 90% or less by weight of the composition, or 75% or less by weight of the composition. In other embodiments, additives suitable for use in the compositions of the present disclosure may be included in an amount of from about 75% to about 99% by weight of the composition. In other embodiments, additives suitable for use in the compositions of the present disclosure may be included in an amount of from about 10% to about 20% by weight of the composition.

The compositions of the present disclosure may further include pharmaceutically acceptable auxiliary substances or adjuvants, including, without limitation, pH adjusting and buffering agents and/or tonicity adjusting agents, such as, for example, citrate, sodium acetate, sodium lactate, sodium chloride, potassium chloride, calcium chloride, etc. Similarly, the compositions of the present disclosure may contain pharmaceutically or nutritionally acceptable carriers and excipients including microspheres, microcapsules, nanoparticles or the like.

In certain embodiments, the dry powder composition may be reconstituted and the resulting reconstituted powder may have a pH greater than 3.0, preferably greater than 3.5 and most preferably greater than 4.0. Reconstitution may be done by introducing a solvent, such as water or an acidic compound, to the dry powder composition to form the reconstituted formulation. This formulation may be usable with liquid aerosolizers, nebulizers, injectables (e.g. parenteral, intradermal, subcutaneous, intramuscular, intraosseous, intraperitoneal, intravenous) oral liquid dosage forms (e.g. syrup, oral suspension, oral solution, oral drop, oral emulsion, mixture, linctuse, elixir), and/or other administration techniques.

An inhalation powder composition of the present disclosure may be delivered to a subject by any means so long as the solid particles of the dry powder composition are capable of being inhaled by a subject so that the particles reach the lungs to permit penetration into the upper and lower airways. In certain embodiments, a dry powder composition of the present disclosure may be delivered to a subject by placing the dry powder within a suitable dosage receptacle in a sufficient amount. Suitable dosage receptacles include those used in reservoir devices (e.g., devices that contain more than one dose in which the device itself meters the dose) or factory-metered dose devices (e.g., devices in which each dose is contained in either a single unit or multiple units). In one example, a suitable reservoir device may have a dosage receptacle that fits within a suitable inhalation device to allow for the aerosolization of the dry powder composition by dispersion into a gas stream to form an aerosol and then delivering the aerosol so produced from a mouthpiece attached for subsequent inhalation by a subject in need of treatment. Such a dosage receptacle includes any container enclosing the composition known in the art such hydroxypropyl methyl cellulose or polymer capsules with a removable portion or body that can be cut or pierced that allows dispersal of the dry powder composition (e.g., via a gas stream directed into the container and via centrifugal force). Such containers are exemplified by those shown in U.S. Pat. No. 4,227,522, U.S. Pat. No. 4,192,309, and U.S. Pat. No. 4,105,027, the entire contents of which are hereby incorporated by reference.

Suitable containers also include those used in conjunction with Plastiape's RS series of inhalers, GlaxoSmithKline's Ventolin Rotahaler brand powder inhaler and/or Fisons' Spinhaler brand powder inhaler. Another suitable unit-dose container which provides a superior moisture barrier is formed from an aluminum foil plastic laminate. The powder composition is filled by weight or by volume into the depression in the formable foil and hermetically sealed with a covering foil-plastic laminate. Such a container for use with a powder inhalation device is described in U.S. Pat. No. 4,778,054 and is used with GlaxoSmithKline's Diskhaler (U.S. Pat. Nos. 4,627,432; 4,811,731; and 5,035,237), the entire contents of which are hereby incorporated by reference. Another such container and powder inhalation device including a vibrating mechanism is described in U.S. Pat. No. 9,132,246, the entire contents of which are hereby incorporated by reference. Yet another suitable delivery system would be a single use disposable device where the dry powder is pre-packaged within the device. In other embodiments, a dry powder composition of the present disclosure may be delivered to a subject via a tracheal tube.

In some embodiments, compositions of the present disclosure may be prepared by spray drying an oil-in-water emulsion containing cannabinoids or other lipophilic ingredients and pharmaceutically acceptable carrier(s) under conditions sufficient to provide a respirable dry powder composition. In some embodiments, the dry powder composition is substantially amorphous.

Dry powder formulations are often prepared by spray drying. Spray drying of the formulations is carried out, for example, as described in the "Spray Drying Handbook", 5$^{th}$ ed., K. Masters, John Wiley & Sons, Inc., NY, N.Y. (1991) and in Platz, R. et al., U.S. Pat. No. 6,592,904, the entire contents of which are hereby incorporated by reference. Generally speaking, spray drying is a process in which a mixture, suspension, or hybrid of soluble and insoluble ingredients and excipients is atomized via a nozzle to form fine droplets which are introduced into and mixed with a hot gas or other fluid stream. For the atomization process, methods such as rotary atomization, pressure atomization and two-fluid atomization can be used. Examples of suitable devices are disclosed in U.S. Pat. No. 6,372,258, the entire contents of which are hereby incorporated by reference. The mixture prepared for spray drying, or annex solution, may be an emulsion, a solution, suspension, slurry, or the like, but care must be taken such that its constituents uniformly distributed and, ultimately, the powdered composition. Preferably the aqueous mixture is a solution. In some embodiments, the aqueous mixture may have a solids content of at least 1% by weight water. In other embodiments, the aqueous mixture may have a solids content of at least 2% by weight water. In other embodiments, the aqueous mixture may have a solids content of at least 4% by weight water. The solvents, water, and terpenes, evaporate from the droplets producing a dry powder containing the lipophilic ingredient and any excipients. The powder is pneumatically conveyed via ducts from the drying chamber to a collection system where it is separated from the drying gas stream. Suitable powder collection systems include bag house type filters, cyclones, and electrostatic separators.

In some embodiments, the spray drying is done under conditions that result in a substantially amorphous powder of homogeneous constitution having a particle size that is respirable, has a low moisture content, and has characteristics that allow for ready aerosolization. In some embodiments, the particle size of the resulting powder is such that more than about 95% of the mass is in particles having a diameter of about 10 μm or less. Powder production by spray drying may be scaled-up from lab to pilot-scale batch sizes. The process can produce up to kilogram quantities of powder per day at high yield (>80%) and with no loss in purity and little to no loss in potency (<5%).

By increasing the percentage of solids in the annex solution (nanoemulsion), other dry powder cannabinoid compositions suitable for oral delivery forms, incorporation into edibles, or for long term storage at room temperature, can be produced at high yields (85-99%) by spray drying, or more preferably by granulation. Such powders exhibit excellent chemical stability and good flow properties. The optical particle size distribution for such powders is in the 5-100 μm range. Ingredients suitable for producing a 100 g batch of such a powder may include, for example, leucine (8 g), trehalose (70 g), d-limonene (48 g), DSPC (3.5 g), citrate (0.5 g) supercritically extracted cannabis oil containing 30% CBD (or another lipophilic substance) (18 g), and water (400 g).

In some embodiments, dry powder compositions may be prepared by other processes such as lyophilization and jet milling as disclosed in WO 91/16038, the entire disclosure of which is hereby incorporated by reference. A number of formulation and processing strategies may be useful to improve, among other things, the storage and stability properties of the dry powder cannabinoid compositions of the present disclosure. In certain embodiments, the cannabinoids used may be chosen to be of a higher purity. In other embodiments, steps may be taken to avoid oxidation of cannabinoids. For example, processing and packaging of the composition may be performed under argon or nitrogen. Similarly, in some embodiments the processing and packaging may be performed to minimize exposure to direct light. Such steps may reduce light-mediated degradation of cannabinoids. In some embodiments, steps such as post spray drying treatment in a vacuum oven may be taken to reduce the amount of moisture or residual terpenes in the composition. Such steps may be useful to avoid hydrolysis, deamidation, and/or oxidation of cannabinoids or other lipophilic actives. As mentioned above, a carbohydrate bulking agent or encapsulation additives may be added to the composition, which also may improve chemical stability.

Furthermore, while the dry powder lipophilic drug substance compositions of the present disclosure have many advantageous properties in certain embodiments. One particularly advantageous property is that the compositions may have a pharmacokinetic profile that is favorable for treatments where rapid uptake and rapid onset of effect is desirable and/or where a prolonged high concentration of drug in the lung or bloodstream is preferable. Advantages in the in vivo pharmacokinetic profiles of cannabinoids, e.g. CBD, THC, CBN, as described in the examples given in this invention, whereby referring to a specific cannabinoid, may be assumed to be similarly advantageous for other cannabinoids.

For example, in certain cannabinoid embodiments, therapeutic value (plasma concentrations of between approximately 10 and 200 ng/mL) is achieved within 4 to 8 minutes after administration via inhalation. The maximum concentration of THC—COOH (Tmax) may be less than or equal to about 30 minutes, less than or equal to about one hour, or less than or equal to about six hours. In some embodiments, median Tmax may be between about three minutes and three hours. Similarly, in certain embodiments, the median amount of time necessary for blood plasma levels of a subject to decrease to one half of the total maximum concentration of THC—COOH ($T_{1/2}$) may be greater than two hours. In some embodiments, $T_{1/2}$ may be about three hours.

In certain embodiments, upon administration of a dry powder THC composition to a subject, the mean maximum blood plasma concentration of THC—COOH (Cmax) may be within the range of about 50% to about 150% of about n×70 ng/mL, wherein n represents a factor to be multiplied and may be a value from 0.01 to 10 and when n =1, the dose is 1 mg.

In one particular embodiment, a dry powder composition having THC present in an amount of about 1 mg may provide a mean maximum blood plasma concentration of THC—COOH within the range of about 50% to about 150% of about 70 ng/mL as measured following a single pulmonary administration. As would be recognized by one of skill in the art, for dry powder compositions containing lower or higher concentrations of THC than 1 mg, the above ranges may be adjusted directly proportionally by the dose. Accordingly, in certain embodiments the present disclosure also provides compositions where the THC or other cannabinoid is present in the dry powder composition in an amount of about n×1 mg. The dry powder composition provides a mean maximum blood plasma concentration of THC—COOH (Cmax) within the range of about 50% to about 150% of about n×70 ng/mL. The maximum blood plasma concentration of THC-COOH is measured following a single pulmonary administration of the dry powder composition where n represents a factor to be multiplied and may be a value from 0.01 to 10.

In some embodiments, the dry powder cannabinoid compositions of the present disclosure may provide average delivery efficiencies (DEs) (ED*FPF) between 40% and 90%. In other embodiments, the dry powder cannabinoid compositions of the present disclosure may provide average delivery efficiencies between 70% and 90%. Delivery efficiency is the emitted dose (ED) (%) (i.e., the amount of the dry powder that exits the inhaler as a percentage of the initial amount of the dry powder present in the capsule) multiplied by the fine particle fraction (%) (i.e., respirable amount or the amount of the dry powder having a MMAD of 5.8 μm or less as a percentage of the emitted dose). In other words, ED is equivalent to (powder mass packaged in capsule—residual powder mass in capsule after actuation—residual powder mass on inhaler)/(powder mass packaged in capsule).

In some embodiments, the dry powder cannabinoid compositions of the present disclosure may provide a bioavailability of 40% or more. Bioavailability is herein defined fraction of a packaged dose of drug that reaches the systemic circulation by either pulmonary, mucosal, or gastrointestinal absorption.

Compositions of the present disclosure may be administered to a subject via pulmonary administration in an amount effective to achieve the desired cannabinoid concentration in the blood. Administration of an effective amount of a composition of the present disclosure may be useful in pharmaceutical, medicinal, and recreational cannabis applications.

As will be recognized by one of ordinary skill in the art, the effective amount needed to treat a particular condition or disease state will depend on the individual, the condition, length of treatment, the regularity of treatment, the type of cannabinoid(s) used, and other factors, but can be readily determined by one of ordinary skill. The patient can achieve a desired dosage by inhaling or otherwise administering an appropriate amount of the composition.

FIG. 1 depicts a flowchart of a process 100 for manufacturing a flowable and dispersible powder. At block 102, the process 100 may include solubilizing a lipophilic substance in a terpene or other organic solvent to form a mixture or mixing an insoluble or slightly soluble substance (which may include, but are not limited to, lipophilic substances such as cannabinoids) into a terpene to form a suspension. As noted above, as used herein slightly soluble substances can be defined as one part solute in 100-1000 ml of solvent and practically insoluble substances are defined as one part solute in greater than 10,000 ml solvent. The lipophilic (or insoluble or slightly soluble) substance may include a cannabinoid, budesonide, ciclesonide, cyclosporine, fluticasone, formoterol, mometasone furoate, mycophenolate, rapamycin, salmeterol, tacrolimus, tiotropium, vilanterol trifenatate, and/or derivatives or analogues thereof. Possible cannabinoids include, without limitation, tetrahydrocannabinol (THC), tetrahydrocannabinolic acid (THCa), cannabidiol (CBD), cannabidiolic acid (CBDa), cannabinol (CBN), cannabichromene (CBC), and/or cannabigerol (CBG), cannabigerivarin (CBGV), tetrahydrocannabivarin (THCV), cannabidivarin (CBDV), cannabichromevarin (CBCV), cannabichromenenic acid (CBCa), cannabigerovarinic acid (CBGVa), tetrahydrocanabivarinic acid (THCVa), cannabidivarinic acid (CBDVa), and/or cannabichromevarinic acid (CBCVa). In some embodiments, the cannabinoid may include synthesized 11-hydroxy-Δ9THC (11-OH-THC) and/or a synthesized metabolite of one or more cannabinoid drug substances. In some embodiments, the insoluble or slightly soluble substance may include a drug that has an ester, amide, imine, acetal, sulphate, or phosphate ester bond, making the insoluble or slightly soluble substance susceptible to hydrolysis during formulation and spray drying from an aqueous solution. In some embodiments, the insoluble or slightly soluble substance comprises one or more of digoxin, diazepam, heparin, hydrocortisone sodium phosphate, a β-lactam, penicillin, a cephalosporin, acetylsalicylic acid, salicylic acid, enalapril, a Type I statin, simvastatin, procaine, lidocaine, methylphenidate, or co-phenotrope (diphenoxylate/atropine).

At least one functional excipient may be added to water to form an aqueous solution at block 104. The mixture or suspension may be dispersed into the aqueous solution using a homogenizer or ultrasonic device at block 106 to form a coarse emulsion. The coarse emulsion may then mixture may then be treated with an ultrasonic or high shear device at block 108 to help form the emulsion with nano-sized oil particles. The terpene may help the lipophilic substance form nano-sized oil droplets in the emulsion. The terpene may include d-limonene, other limonenes, beta-myrcene, and/or other terpenes. In some embodiments, the aqueous solution may include at least one functional excipient. Functional excipients may include, for example, hydrophobic amino acid, a disaccharide, an oligosaccharide, a surfactant, an emulsifier, a stabilizing additive, and/or a bulking agent. The nanoemulsion may be spray dried at block 110, thereby evaporating at least a portion of the terpene and substantially all of the water to form a dry powder formed from solid particles that include the lipophilic substance and/or the insoluble or slightly soluble substance. As used herein, substantially all may mean that at least 93% of the water is evaporated, in some cases at least 96% of the water is evaporated, and in other cases at least 98% of the water is evaporated. Such dry powder may be administered using a dry powder inhaler and/or be reconstituted for use in other administration techniques. In some embodiments, the insoluble or slightly soluble substance may be sensitive to hydrolysis. In such cases the terpene serves as a protective processing intermediate during the spray drying and/or granulation process.

In some embodiments, the dry powder composition may have a moisture content below about 10% by weight water, with a preferred range between 1 and 6%. The dry powder composition may include between about 0.1% and 30% by weight of cannabinoid component. The dry powder composition may have a tap density between about 0.1 g/cm and 0.4 g/cm. In some embodiments, the dry powder composition may include a hydrophobic amino acid, a disaccharide, a oligosaccharide, a surfactant, an emulsifier, a stabilizing additive, and/or a bulking agent. The hydrophobic amino acid may include tryptophan, tyrosine, leucine, dileucine, trileucine, and/or phenylalanine. Surface modifying and flow enhancing agents may include hyaluronic acid, polyethyleneglycol, hydroxypropylmethylcellulose (HPMC) , and/or methylcellulose (MC). In other embodiments, the bulking agent may include lactose, mannitol, trehalose, raffinose, and/or maltodextrins. In some embodiments, the stabilizing additive includes a non-ionic detergent, a non-ionic block copolymer, an ionic surfactant, phospholipids, citrates, polysorbates, sorbitan laurate, polyglyceryl-4 laurate, and/or cyclic oligosaccharisdes.

In some embodiments, the insoluble or slightly soluble substance may have a median geometric diameter ranging from 0.01 μm to about 50 μm, more preferably between about 0.01 μm to about 20 μm. In some embodiments, the dry powder may include between about 1% and 60% by weight of a cannabinoid, more typically between about 21% and 60%.

In some embodiments, the dry powder formed above may be further processed. For example, the dry powder may be processed via a wet granulation process to form granules offering homogenous drug distribution throughout the powder and having a median granule diameter between 0.05 mm and 3 mm. For example, a previously spray dried cannabinoid powder may be charged into a chamber of a granulator. In some embodiments, a wetting agent used in the wet granulation process may be aqueous and contains a binding agent. The wetting agent can be pumped into the contents of the chamber in a high shear type granulator, can be sprayed onto the powder in a fluidized bed granulator, and/or may be otherwise introduced into the chamber. In some embodiments, the wetting agent is formulated to contain an enteric coating and/or other excipients known to alter pharmacokinetic properties. For example, in some embodiments the wetting agent may include CEL, Cyclodextrins,Tween 80, Solutol HS 15, and/or Poloxamer 188. The wetting agent may include at least functional excipient and at least one cannabinoid drug substance. The binding agent may include microcrystalline cellulose. It will be appreciated that other processing using wet granulation processes is possible in some embodiments.

FIG. 2 shows a flowchart of a process 200 of manufacturing a flowable and dispersible powder. Process 200 may be similar to process 100, and may include similar steps and include similar chemical components. At block 202, process 200 may include dissolving a lipophilic ingredient in an organic solvent to form a lipophilic phase. The lipophilic ingredient may include one or more of a cannabinoid (which may be a naturally derived cannabinoid a synthetically derived cannabinoid, and/or a combination thereof), budesonide, ciclesonide, cyclosporine, fluticasone, formoterol, mometasone furoate, mycophenolate, rapamycin, salmeterol, tacrolimus, tiotropium, vilanterol trifenatate, and/or derivatives or analogues thereof. The lipophilic ingredient may also, or alternatively, include an extract of hops, an extract of sage (Salvia officinalis/lavandulaefolia), rosmarinic acid, a polyphenolic compound, caffeic acid, and/or nicotine. In some embodiments, the lipophilic ingredient includes at least two of the above substances. In some embodiments, each of the lipophilic substances is encapsulated in a unique domain, while in other embodiments, the multiple lipophilic substances are encapsulated in domains as a mixture. Improved delivery efficiency of combination therapeutics may be possible with the approach presented herein. It may also present a new pathway to repurpose existing drugs or offer new processing options to address past formulation problems. Optionally, formulating combination products in this manner could enable multiple drugs (dual, triple, and so on) to be processed in separate lipophilic fractions which may limit or prevent degradation due to chemical incompatibility. In cases where lipophilic and hydrophilic combinations are desired, the respective fractions may be formulated and spray dried to produce a single particle of the combination drugs. Still in other cases an insoluble or slightly soluble micronized drug could be introduced to the lipophilic fraction to segregate it from chemically incompatible active or inactive components. Examples of combination products (two or more APIs) include Combivent Respimat® (albuterol+ipratropium), Advair Diskus® (fluticasone+salmeterol), Symbicort HFA® (budesonide+formoterol), Utibron™ Neohaler® (indacaterol+glycopyrronium), and Flutiform® (fluticasone propionate+formoterol fumarate). The organic solvent may include a terpene, such as d-limonene, other limonenes, and/or beta-myrcene. Other organic solvents may include an alcohol such as ethanol or methanol. In some embodiments, the lipophilic ingredient is combined with the organic solvent in a ratio of less than 1.0 by weight.

At block 204, at least one of a surfactant or an emulsifier is dissolved in the lipophilic phase. Emulsifiers may include non-ionic detergents, nonionic block copolymers, ionic surfactants, and/or combinations thereof. Other emulsifiers may include phospholipids, polysorbates, sorbitan laurate, polyglyceryl-4 laurate, dylauryl citrate, and/or combinations thereof. In some embodiments, the emulsifier may include a cyclic oligosaccharide, such as an alphadextrin and/or beta-cyclodextrin. At block 206, one or more excipients are dissolved into water to form an aqueous phase. Stability of the nanoemulsion may be enhanced by adjustments to pH by the introduction excipients such as citrate or sodium citrate. The lipophilic phase is dispersed into the aqueous phase at block 208 to form an emulsion that includes nano-sized oil droplets. This dispersing may include the use of ultrasonic homogenization and/or high pressure/high shear homogenization. In some embodiments, the emulsion may be formed in a continuous, inline manner such that emulsifiers are not required. Such an emulsion may be rapidly fed into a spray dryer. The nanosized droplets have a droplet size $d_{50}$ between about 20 nm and 1 μm, a droplet size $d_{50}$ between about 20 and 500 nm, or a droplet size $d_{50}$ between about 50 and 300 nm.

The emulsion may include a matrix forming excipient. Matrix forming excipients may include an oligosaccharide, such as inulin. In some embodiments, the matrix forming excipients include a saccharide and/or a polysaccharide. The emulsion may further include an encapsulating excipient, such as an amino acid like leucine.

The emulsion may be spray dried to form a dry powder that includes the lipophilic ingredient at block 210. The emulsion may also be sonified with an ultrasonic horn operating in pulse mode. Droplets formed during the spray drying may be atomized using a multi-fluid atomizer and at least one fluid utilized by the multi-fluid atomizer may be a compressed gas. In some embodiments, the dry powder includes between about 0.01% and 50% w/w of the lipophilic ingredient.

FIG. 3 depicts a flowchart of a process 300 of manufacturing a flowable and dispersible powder, similar to processes 100 and 200 described above. Process 300 may include mixing an oil solution with a water solution (or other solvent) to form an oil-in-water emulsion composition at block 302. The oil solution may include a cannabinoid or other lipophilic ingredient. The oil-in-water emulsion composition may include at least one of a hydrophobic amino acid, a disaccharide, and/or a oligosaccharide. The oil-in-water emulsion composition may be spray dried to form a dry powder composition at block 304. This dry powder composition may be administered, such as by pulmonary inhalation, in the treatment of a number of systemic and/or lung conditions.

To facilitate a better understanding of the present invention, the following examples of certain aspects of some embodiments are given. In no way should the following examples be read to limit, or define, the entire scope of the invention. Additionally, the processes for manufacture and administration of the dry powder compositions described herein may include additional steps, have steps omitted, and/or steps combined.

EXAMPLE 1

An annex solution (feedstock) for spray drying into dry powder was prepared in two portions: a lipophilic phase preparation and an aqueous phase preparation. The preparation of the lipophilic phase involved dissolving a lipophilic active ingredient (hops oil extract) into an organic solvent (d-limonene) followed by dissolving a surfactant (emulsifier) into the lipophilic/solvent mixture. The aqueous phase preparation involved selecting excipients (e.g. amino acids, carbohydrates, disaccharides, oligosaccharides, cellulose) and dissolving these excipients into water at or near 20° C., or at higher temperatures depending on excipient solubility.

Figure 4:
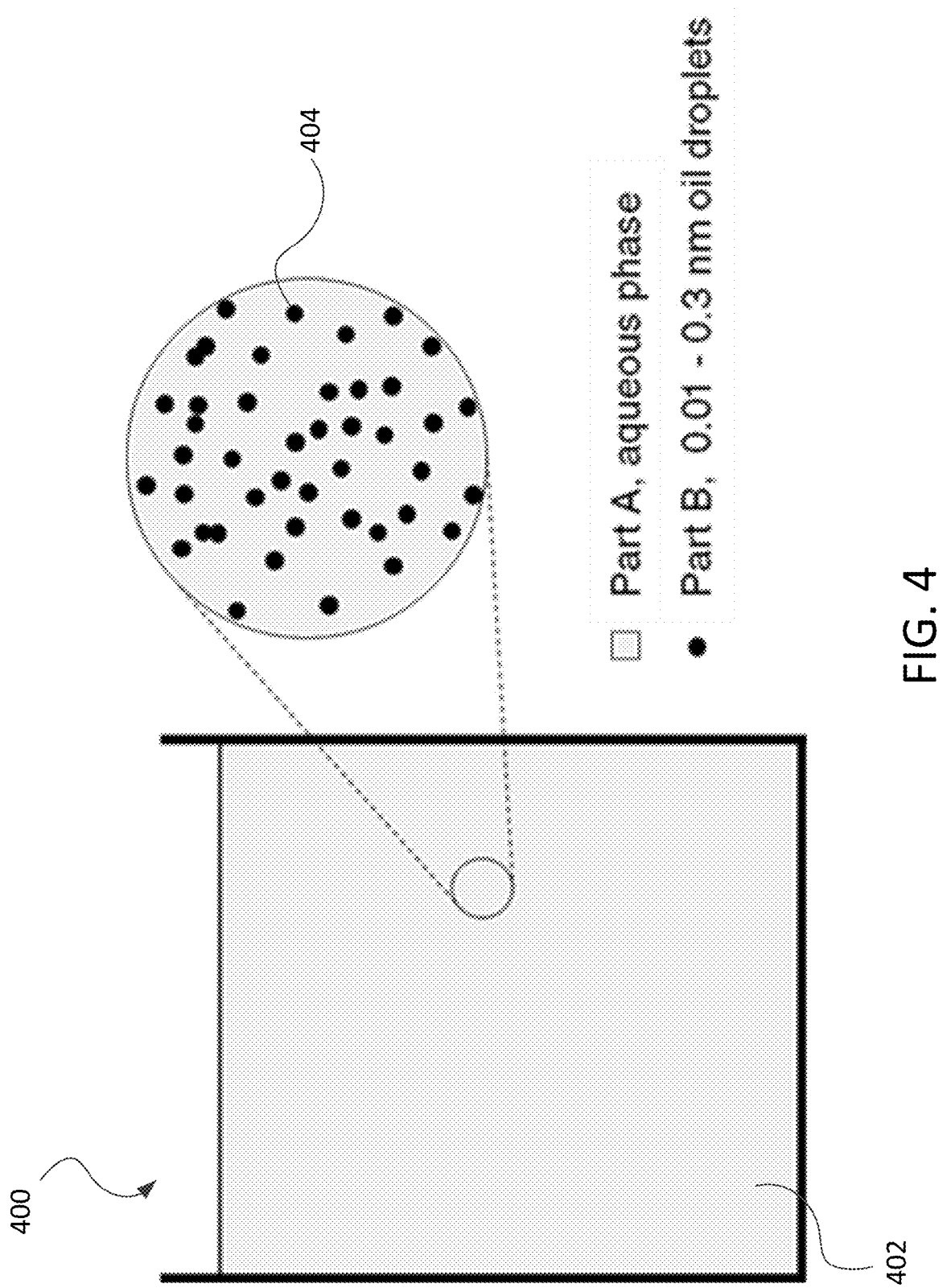
FIG. 4 depicts a schematic of an annex solution that was prepared for spray drying according to embodiments.
Figure 5:
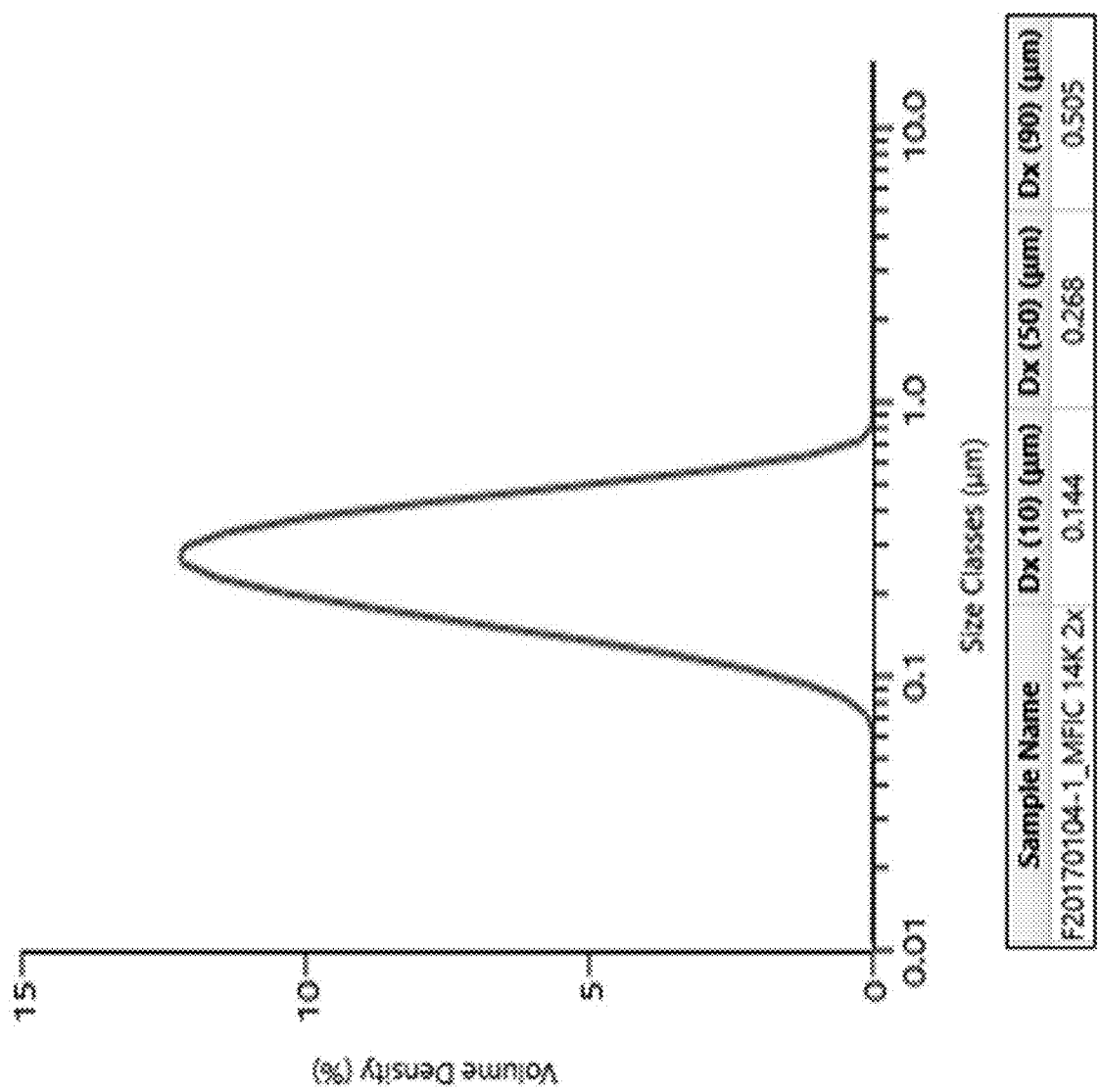
FIG. 5 depicts a graph of a droplet size distribution after processing into a nanosized oil-in-water emulsion according to embodiments.

The lipophilic phase preparation was dispersed into the aqueous phase preparation to form an emulsion 400 that includes nanosized oil droplets 402 distributed within aqueous phase preparation 404 as shown in FIG. 4. The majority of oil droplets 402 ranged between about 0.01 nm and 0.3 nm. The particle size distribution for the oil droplets 402 as determined by Malvern Mastersizer 3000 with HydroMV is shown in FIG. 5. The particle size distribution included the following values: $D_{10}$ (um)=0.103; $D_{50}$ (um)=0.205; and $D_{90}$ (um)=0.453. The emulsion containing nano-particles was formed using common practices such as ultrasonic and/or high pressure homogenizer techniques. The resultant annex solution was spray dried into dry powder which had $D_{10}$ (um)=1.0; $D_{50}$ (um)=2.2; and $D_{90}$ (UM)=4.1. Capsules filled with powder (10 mg target) were aerosol tested (ACI at 28.3 lpm) with the RS01 inhaler were found to have MMAD (um)=3.3, FPF=85%, and DE=73%.

"Active substances" or "active ingredient" as described herein includes a lipophilic agent, drug, compound, composition of matter or mixture thereof which provides some pharmacological, nutraceutical, or nutritional action.

EXAMPLE 2

As in Example 1, an annex solution (feedstock) for spray drying into dry powder was prepared in two portions: a lipophilic phase preparation and an aqueous phase preparation. The preparation of the lipophilic phase involved dissolving a lipophilic active ingredient into an organic solvent followed by adding a surfactant (emulsifier) into the lipophilic/solvent mixture. The aqueous phase preparation involved selecting excipients (e.g. amino acids, carbohydrates, disaccharides, oligosaccharides, cellulose, acids) and dissolving these excipients into water at or near 20° C., or at higher temperatures depending on excipient solubility.

The aqueous and lipophilic preparations were heated to between about 60° C. and 70° C. The lipophilic phase preparation was then dispersed into the aqueous phase preparation to form an emulsion 400 that includes nanosized oil droplets 402 distributed within aqueous phase preparation 404. The majority of oil droplets 402 ranged between about 0.01 nm and 0.3 nm. The droplet size distribution as measured by Malvern Mastersizer 3000 with HydroMV included the following values: $D_{10}$ (um)=0.2; $D_{50}$ (um)=0.3; and $D_{90}$ (um)=0.5. The emulsion containing nano-particles was formed using common practices such as ultrasonic and/or high pressure homogenizer techniques. The resultant annex solution was spray dried into a dry powder (7.5% oil extract content) which had $D_{10}$ (um)=0.8; $D_{50}$ (um)=2.0; and $D_{90}$ (um)=4.0. Capsules filled with powder (10 mg target) were aerosol tested (ACI at 28.3 lpm) with the RS01 inhaler had MMAD(um)=2.5, FPF=95%, and DE=89%.

"Active substances" or "active ingredient" as described herein includes a lipophilic agent, drug, compound, composition of matter or mixture thereof which provides some pharmacological, nutraceutical, or nutritional action.

EXAMPLE 3

Figure 6:
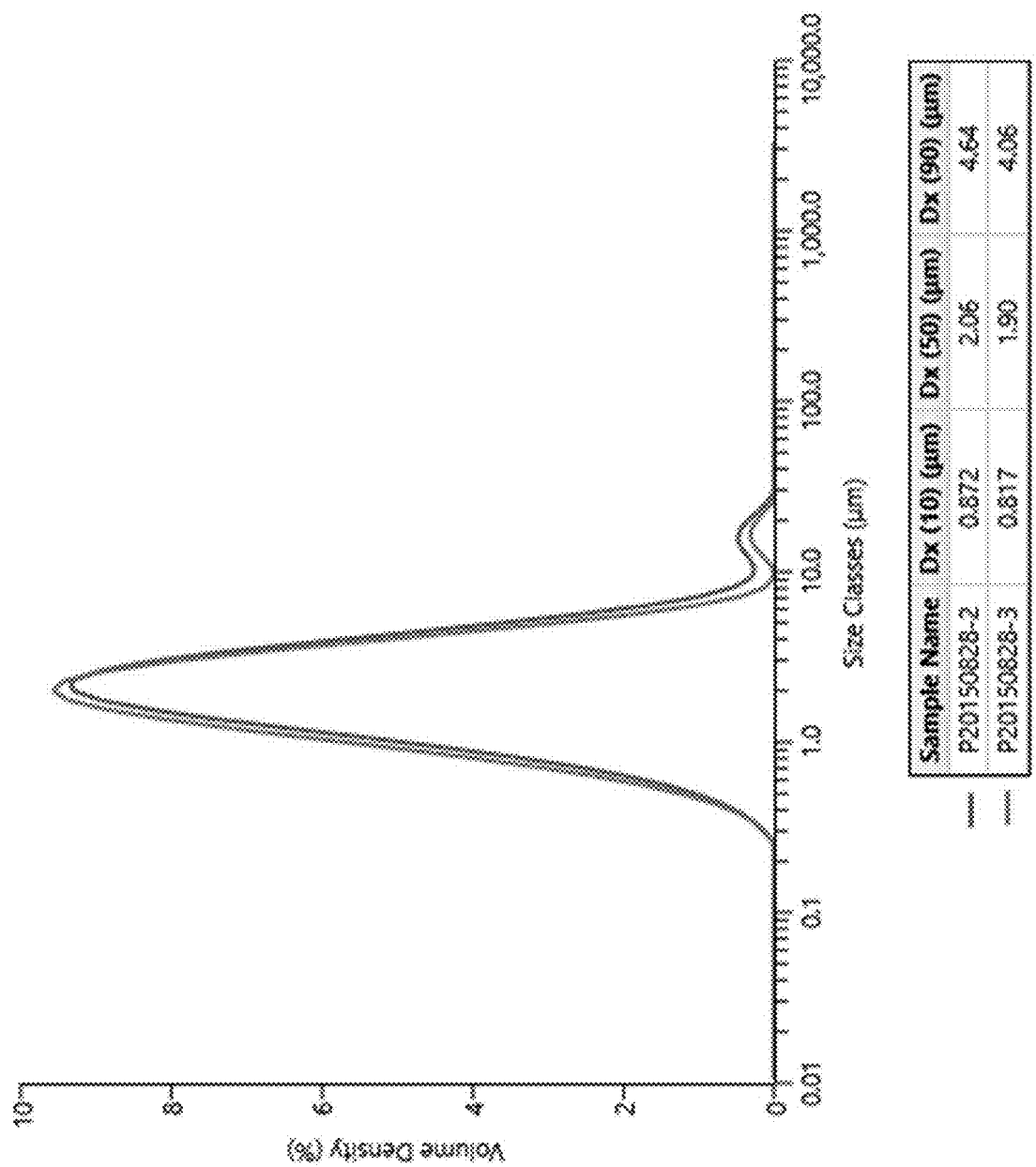
FIG. 6 is a plot of an optical particle size distribution of powders spray dried for pulmonary delivery according to embodiments.
Figure 7:
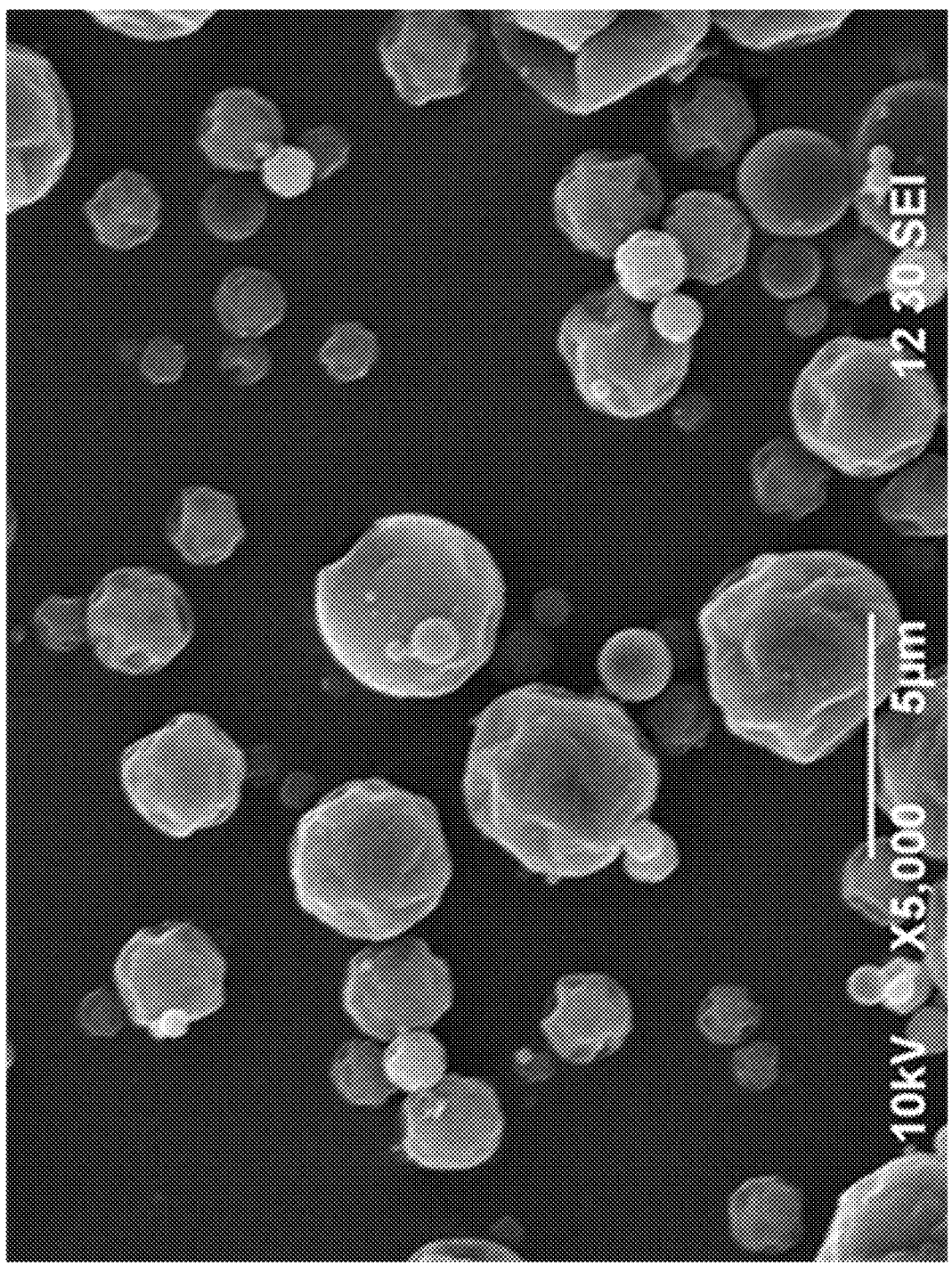
FIG. 7 is a scanning electron microscopy image of spray dried particles containing cannabinoids according to embodiments.

Dry powder cannabinoid compositions suitable for pulmonary delivery were produced using a spray dryer at high yield (80-90%) and at 5 g batch sizes. These powders exhibited very good aerosol performance when actuated via the RS01 inhaler (Plastiape, Italy) as evidenced by mean DE of 68% and fine FPF of 83% as determined by Anderson Cascade Impactor (ACI). Particle size distribution for two batches of spray dried powder is depicted in FIG. 6. The particle size distribution included the following values for the first batch: $D_{10}$ (um)=0.9; $D_{50}$ (um)=2.1; and $D_{90}$ (um) =4.6. The particle size distribution included the following values for the second batch: $D_{10}$ (um)=0.8; $D_{50}$ (um)=1.9; and $D_{90}$ (um)=4.1. Particle size distribution was very consistent across the two batches. A scanning electron micrograph showing particle appearance is shown in FIG. 7.

Ingredients for producing a dry powder composition having approximately 6.4% by weight cannabinoid active ingredient include leucine (2.9 g), inulin (1.0 g), HPMC (0.15 g), d-limonene (1.1 g), Plantamulse™ (0.4 g), supercritically extracted cannabis oil containing 90% THC (0.3 g), and water. The emulsion (annex solution) was prepared in accordance with the process of Example 1.

A Production Minor (GEA Group, DE) with custom high efficiency cyclone was used to generate and collect the powder. The equilibrium drying condition was established using de-ionized water. When stable operation was achieved, the nozzle input was switched to annex (feedstock) solution. The solution was fed to the dryer until it was depleted and then the nozzle was switched back to water for approximately 5 minutes to clear the system. The collector containing dry powder was exchanged for a clean collector and the dryer was then shut down. The filled collector was rapidly capped on removal to minimize exposure to room humidity. The filled collector was transferred into a low humidity glove box purged with clean dry air or nitrogen where the powder was transferable into other vessels for storage or into capsules and/or other unit dose packets.

EXAMPLE 4

A carbohydrate bulking agent was included in an oil extract-leucine formulation. The addition of trehalose as a carbohydrate bulking agent can improve the chemical stability of dry-powder cannabinoid compositions of the present disclosure. Additionally, trehalose and DSPC were inserted in the powder formulation based on their inclusion in DPI products approved by the FDA, e.g TOBI® PodhalerTM (Novartis, AG).

Figure 8:
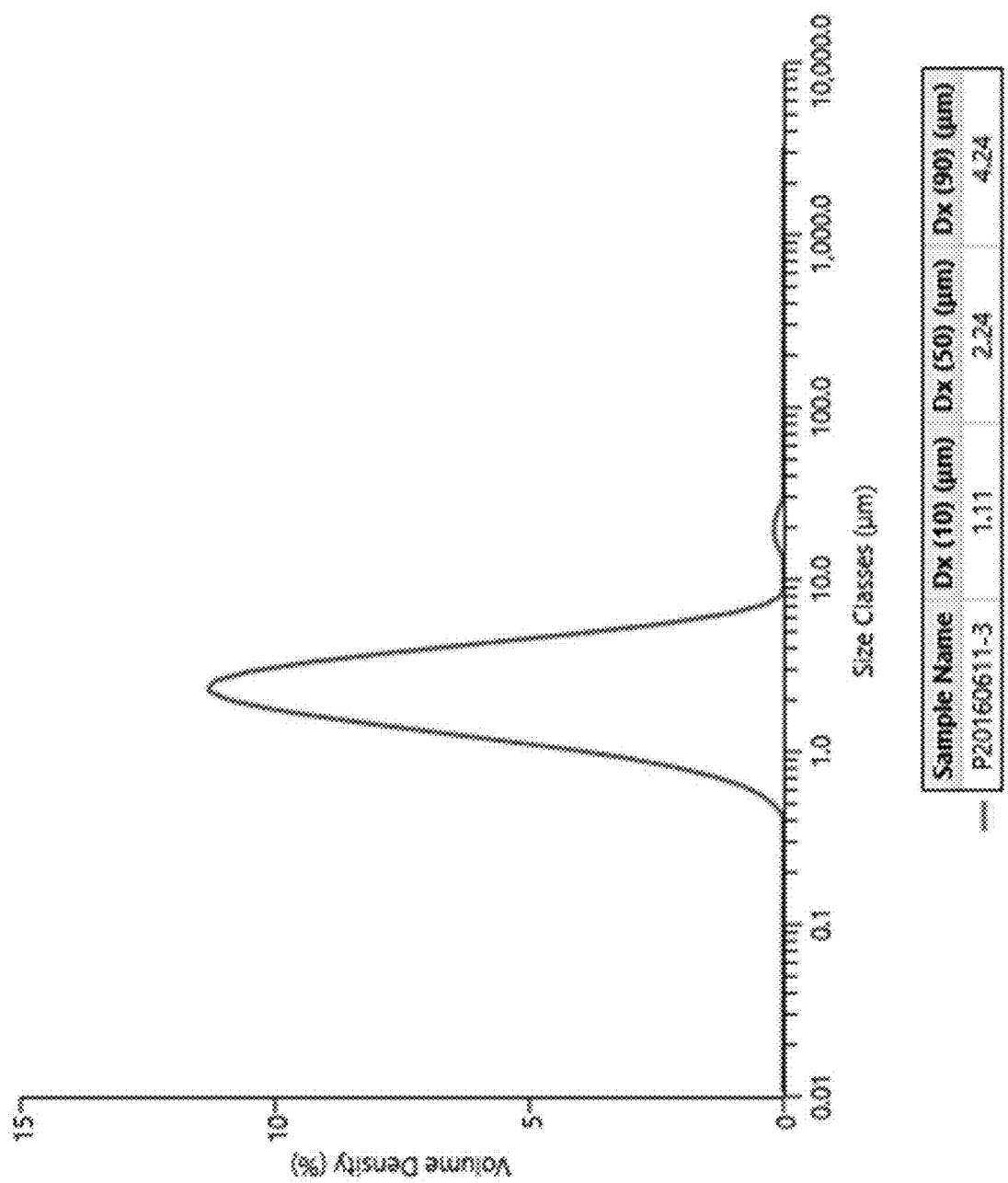
FIG. 8 is a plot of an optical particle size distribution of powders spray dried for pulmonary delivery according to embodiments.

Dry powder oil extract compositions suitable for pulmonary delivery were produced using a Mobile Minor (GEA Group, DE) spray dryer. Capsules filled with these powders (10 mg target) had an MMAD of 2.3 μm and exhibited excellent aerosol performance when actuated via the RS01 inhaler (Plastiape, Italy) as evidenced by FPF of 93% and DE of 90%. The particle size distribution for the spray dried powder is depicted in FIG. 8. The particle size distribution included the following values: $D_{10}$ (um)=1.1; $D_{50}$ (um)=2.2; and $D_{90}$ (um)=4.2.

Ingredients for producing a dry powder composition having approximately 12% by weight active ingredient include leucine (80%), trehalose (6.5%), DSPC (1.5%), and supercritically extracted oil (12%). Water and d-limonene were used as solvents. The emulsion (annex solution) was prepared in accordance with the process of Example 1.

EXAMPLE 5

A carbohydrate bulking agent was included in a cannabinoid-leucine formulation. The addition of trehalose as a carbohydrate bulking agent can improve the chemical stability of dry-powder cannabinoid compositions of the present disclosure. Additionally, trehalose has been incorporated in powder for pulmonary administration products approved by the FDA, e.g TOBI® Podhaler™ (Novartis, AG).

Dry powder cannabinoid compositions suitable for pulmonary delivery were produced using a Mobile Minor (GEA Group, DE) spray dryer. These powders exhibited very good aerosol performance when actuated via the RS01 inhaler (Plastiape, Italy) as evidenced by mean DE of 68% and fine FPF of 83% as determined by Anderson Cascade Impactor (ACI operated at 28.3 lpm). The particle size distribution for the spray dried powder is depicted in FIG. 9. The particle size distribution included the following values: $D_{10}$ (um)=0.5; $D_{50}$ (um)=2.7; and $D_{90}$ (um)=6.0.

Ingredients for producing a dry powder composition having approximately 5% by weight cannabinoid active ingredient include leucine (47%), trehalose (47%), DSPC (1%), and supercritically extracted cannabis crystals containing 99% CBD (5%). Water and d-limonene were used as solvents. The emulsion (annex solution) was prepared in accordance with the process of Example 1.

What is claimed is:
1. A method of manufacturing a flowable and dispersible powder, the method comprising:
   mixing an insoluble or slightly soluble substance into a terpene to form a suspension or solution, wherein the insoluble or slightly soluble substance comprises one or both of a plant derived or synthesized cannabinoid drug substance;
   introducing a surfactant into the suspension or solution, wherein the surfactant comprises di stearoylphosphatidylcholine (DSPC);
   adding at least one functional excipient to water to form an aqueous solution, wherein the at least one functional excipient comprises one or more of leucine and trileucine and one or more of trehalose, mannitol, and inulin;
   dispersing the suspension into the aqueous solution using one or both of a homogenizer or an ultrasonic device to form a coarse emulsion;

treating the coarse emulsion with one or both of the ultrasonic device or a high shear device to form a nanoemulsion; and spray drying the nanoemulsion, thereby evaporating at least a portion of the terpene and substantially all the water to form a dry powder formed from solid particles comprising the insoluble or slightly soluble substance, wherein:

the dry powder comprises between about 1% and 60% collectively by weight of the one or both of a plant derived or synthesized cannabinoid drug substance:

the dry powder has a bulk density of between about 0.05 g/cm$^3$ and 0.30 g/cm$^3$; and the dry powder has a tap density of between about 0.1 g/cm$^3$ and 0.4 g/cm$^3$.

2. The method of manufacturing a flowable and dispersible powder of claim 1, wherein:

the solid particles comprising the insoluble or slightly soluble substance have a median geometric diameter ranging from 0.01 μm to about 50 μm.

3. The method of manufacturing a flowable and dispersible powder of claim 1, wherein:

the solid particles comprising the insoluble or slightly soluble substance have a median geometric diameter ranging from 0.01 μm to about 20 μm.

4. The method of manufacturing a flowable and dispersible powder of claim 1, wherein:

the one or both of a plant derived or synthesized cannabinoid drug substance comprises one or more of synthesized 11-hydroxy-Δ9THC (11-OH-THC) or a synthesized metabolite of one or more cannabinoid drug substances.

5. The method of manufacturing a flowable and dispersible powder of claim 1, wherein:

the insoluble or slightly soluble substance is sensitive to hydrolysis; and the terpene serves as a protective processing intermediate during the spray drying process.

6. The method of manufacturing a flowable and dispersible powder of claim 1, wherein:

each of the coarse emulsion and the nanoemulsion comprises the insoluble or slightly soluble substance is encapsulated within the terpene to protects the insoluble or slightly soluble substance from hydrolysis within the coarse emulsion, the nanoemulsion, and during the spray drying process.

7. A method of manufacturing a flowable and dispersible powder, the method comprising:

mixing an insoluble or slightly soluble substance into a terpene to form a suspension or solution, wherein the insoluble or slightly soluble substance comprises one or both of a plant derived or synthesized cannabinoid drug substance;

introducing a surfactant into the suspension or solution, wherein the surfactant comprises di stearoylphosphatidylcholine (DSPC);

adding at least one functional excipient to water to form an aqueous solution, wherein the at least one functional excipient comprises one or more of leucine and trileucine and one or more of trehalose, mannitol, and inulin;

dispersing the suspension into the aqueous solution using one or both of a homogenizer or an ultrasonic device to form a coarse emulsion;

treating the coarse emulsion with a microfluidizer to form a nanoemulsion; and spray drying the nanoemulsion, thereby evaporating at least a portion of the terpene and substantially all the water to form a dry powder formed from solid particles comprising the insoluble or slightly soluble substance, wherein:

the dry powder comprises between about 1% and 60% collectively by weight of the one or both of a plant derived or synthesized cannabinoid drug substance:

the dry powder has a bulk density of between about 0.05 g/cm$^3$ and 0.30 g/cm$^3$; and the dry powder has a tap density of between about 0.1 g/cm$^3$ and 0.4 g/cm$^3$.

8. The method of manufacturing a flowable and dispersible powder of claim 1, wherein:

the dry powder comprises between about 1% and 60% by weight of 11-hydroxy-Δ9THC (11-OH-THC) as the insoluble or slightly soluble substance.

9. The method of manufacturing a flowable and dispersible powder of claim 1, further comprising:

processing the dry powder using a wet granulation device to form a free flowing powder.

10. The method of manufacturing a flowable and dispersible powder of claim 9, wherein:

processing the dry powder using a wet granulation device comprises:

charging the dry powder into a chamber of the wet granulation device;

introducing a coating and binding agent into the chamber; and drying contents of the chamber to form the free flowing powder.

11. The method of manufacturing a flowable and dispersible powder of claim 7, further comprising:

processing the dry powder using a wet granulation device to form a free flowing powder by:

charging the dry powder into a chamber of the wet granulation device;

introducing a coating and binding agent into the chamber; and drying contents of the chamber to form the free flowing powder.

12. The method of manufacturing a flowable and dispersible powder of claim 11, wherein:

the coating and binding agent comprises a cannabinoid oil-in-water emulsion.

13. The method of manufacturing a flowable and dispersible powder of claim 11, wherein:

the wet granulation device comprises a high shear granulator; and introducing the coating and binding agent into the chamber comprises pumping the coating and binding agent into the chamber.

14. The method of manufacturing a flowable and dispersible powder of claim 11, wherein:

the free flowing powder comprises granules offering homogenous drug distribution throughout the free flowing powder.

* * * * *